United States Patent
Da Silva et al.

(10) Patent No.: US 11,654,093 B2
(45) Date of Patent: *May 23, 2023

(54) MONOPHASIC APPEARANCE COSMETIC HAIR COMPOSITION COMPRISING A PARTICULAR NONIONIC SURFACTANT

(71) Applicant: L'Oreal, Paris (FR)

(72) Inventors: Sylvia Da Silva, Saint Ouen (FR); Aldo Pizzino, Saint Ouen (FR); Ségolène De Menthiere, Saint Ouen (FR)

(73) Assignee: L'Oreal, Paris (FR)

( * ) Notice: Subject to any disclaimer, the term of this patent is extended or adjusted under 35 U.S.C. 154(b) by 277 days.

This patent is subject to a terminal disclaimer.

(21) Appl. No.: 16/772,730

(22) PCT Filed: Dec. 13, 2018

(86) PCT No.: PCT/EP2018/084793

§ 371 (c)(1),
(2) Date: Jun. 12, 2020

(87) PCT Pub. No.: WO2019/115706

PCT Pub. Date: Jun. 20, 2019

(65) Prior Publication Data

US 2020/0315934 A1    Oct. 8, 2020

(30) Foreign Application Priority Data

Dec. 14, 2017   (FR) ........................... 1762107

(51) Int. Cl.
| | |
|---|---|
| *A61Q 5/06* | (2006.01) |
| *A61K 8/34* | (2006.01) |
| *A45D 34/00* | (2006.01) |
| *A61K 8/31* | (2006.01) |
| *A61K 8/49* | (2006.01) |
| *A61K 8/81* | (2006.01) |
| *A61K 8/92* | (2006.01) |
| *A45D 19/00* | (2006.01) |

(52) U.S. Cl.
CPC .............. *A61K 8/342* (2013.01); *A45D 34/00* (2013.01); *A61K 8/31* (2013.01); *A61K 8/4973* (2013.01); *A61K 8/8176* (2013.01); *A61K 8/92* (2013.01); *A61Q 5/06* (2013.01); *A45D 19/0041* (2021.01); *A45D 2200/053* (2013.01); *A45D 2200/057* (2013.01)

(58) Field of Classification Search
CPC . A61Q 5/06; A61K 8/046; A61K 8/86; A61K 8/31; A61K 8/922; A61K 2800/87; A61K 8/39
USPC ........................................................ 424/70.1
See application file for complete search history.

(56) References Cited

U.S. PATENT DOCUMENTS

| | | | |
|---|---|---|---|
| 2003/0108505 A1 | 6/2003 | Cao et al. | |
| 2004/0028632 A1* | 2/2004 | Maillefer | ............... A61K 8/922 424/70.2 |
| 2009/0098079 A1* | 4/2009 | Schiemann | ............ A61K 8/046 424/70.122 |
| 2016/0113857 A1* | 4/2016 | Fondin | ..................... A61K 8/86 424/70.15 |

FOREIGN PATENT DOCUMENTS

| | | | |
|---|---|---|---|
| EP | 0 879 590 A2 | 11/1998 | |
| EP | 0879590 A2 * | 11/1998 | ............... A61Q 5/12 |
| EP | 1 792 600 A1 | 6/2007 | |
| EP | 2 335 674 A1 | 6/2011 | |
| WO | 2016/169957 A1 | 10/2016 | |

OTHER PUBLICATIONS

STIC Search Report dated Apr. 26, 2022.*
International Search Report dated Feb. 13, 2019, issued in corresponding International Application No. PCT/EP2018/084793, filed Dec. 3, 2018, 3 pages.
Natural Mousee Air-Turbo Charged Hair Styling Foam, Company: Giovanni Cosmetics, Record ID: 206581; May 31, 2013, Database GNPD [Online], Mintel, 3 pages.
Thickening Mousse, Company: Living Proof, Record ID: 4619535; Feb. 28, 2017, Database GNPD [Online], Mintel, 2 pages.

* cited by examiner

*Primary Examiner* — Eisa B Elhilo
(74) *Attorney, Agent, or Firm* — Christensen O'Connor Johnson Kindness PLLC

(57) ABSTRACT

The present invention relates to a cosmetic composition having a monophasic appearance, comprising at least one particular non-ionic surfactant, water and at least one propellant. The invention also relates to an aerosol device and also to a process for styling keratin fibres using such a composition.

17 Claims, No Drawings

MONOPHASIC APPEARANCE COSMETIC HAIR COMPOSITION COMPRISING A PARTICULAR NONIONIC SURFACTANT

The present invention relates to a cosmetic composition having a monophasic appearance, comprising at least one particular non-ionic surfactant, water and at least one propellant.

The invention also relates to an aerosol device and also to a process for styling keratin fibres using such a composition.

Styling products are normally used to construct and structure the hairstyle and to give it shape retention. They are usually in the form of lotions, gels, mousses, creams, sprays, etc. These compositions generally comprise one or more film-forming polymers or "fixing polymers". These polymers allow the formation of a coating film on the hair, thus providing form retention of the hairstyle.

Products which are hairstyle or hairstyle shape retention aids and which do not comprise a fixing polymer also exist.

These compositions may be in the form of hair gels, sprays or mousses which are generally applied to wet hair, which is shaped before performing blow drying or drying.

Hairstyling products in aerosol devices are generally available in an opaque container since they do not generally have a sufficiently attractive appearance, in particular in the presence of a propellant, especially in the presence of a liquefied propellant.

Moreover, an increasing number of users of hairstyling products are especially searching for compositions which are more attractive, more fluid or even clearer.

The applicant has now discovered, surprisingly, that a cosmetic composition having a monophasic appearance, comprising one or more particular non-ionic surfactants, water and one or more propellants makes it possible to solve the abovementioned problems.

A subject of the present invention is thus a cosmetic composition having a monophasic appearance, comprising:
i) at least one non-ionic surfactant of formula (I):

$$R-O-(CH_2-CH_2-O)_n-H \quad (I)$$

in which:
R is a linear or branched $C_8$-$C_{40}$ alkenyl radical;
n is an integer ranging from 6 to 20,
ii) water; and
iii) one or more propellants.

The composition according to the invention, when it is propelled by means of a conventional aerosol device, makes it possible in particular to dispense a uniform, firm and creamy foam which holds well in the hand.

Furthermore, the foam formed from the composition according to the invention spreads easily and uniformly on the hair, and has good styling properties. It especially affords good hold of the head of hair over time under both wet and dry conditions, while at the same time giving the head of hair volume, and without making the hairstyle rigid. In the case of curly hair, the composition according to the invention affords good curl definition.

In particular, the composition according to the invention gives the hairstyle a natural look and fluid movement.

It also gives the hair a particularly soft and pleasant feel.

The composition according to the invention is preferably clear, which gives it a particularly attractive aesthetic appearance that is highly sought after by users. The applicant has in particular noted, surprisingly, that the aesthetic appearance of the composition according to the invention is particularly augmented when it is packaged in a container that is itself transparent.

It has also been noted that the composition according to the invention is stable over time. In particular, the appearance of the composition according to the invention remains significantly the same after 2 months of storage at ambient temperature (25° C.).

A subject of the present invention is also an aerosol device comprising a composition according to the invention, a container containing said composition, and a means for spraying said composition.

A subject of the invention is also a process for styling keratin fibres, in particular human keratin fibres such as the hair, comprising the application to said fibres of the composition, this application being optionally followed by rinsing after an optional leave-on-time.

Other subjects, characteristics, aspects and advantages of the invention will emerge even more clearly on reading the description and the example that follows.

In the present description, and unless otherwise indicated:
the expression "at least one" is equivalent to the expression "one or more" and can be substituted for said expression; the expression "between . . . and . . . " is equivalent to the expression "ranging from . . . to . . . " and can be substituted for said expression, and implies that the limits are included.

According to the present application, the term "keratin fibres" denotes human keratin fibres and more particularly the hair.

The expression "free of a cationic group" is intended to mean that the compound does not comprise a cationic group and/or a cationizable function in its chemical structure.

The cosmetic composition according to the present invention has a monophasic appearance. For the purposes of the present invention, the term "monophasic appearance" is intended to mean that the composition according to the invention is constituted, at ambient temperature(25°) and atmospheric pressure:
of a single phase; or
of two or more phases, where one of the phases is dispersed in the other, such that it is not possible to distinguish the phases from one another with the naked eye.

The composition of monophasic appearance according to the invention is advantageously in the form of a clear to translucent, more preferentially clear, fluid. The clarity of the composition according to the invention can be characterized by the measurement of its turbidity, by turbidimetry (in NTU units). In the context of the present invention, the turbidity measurements were carried out with a turbidimeter, model HI 88713-ISO from the company Hanna Instruments.

Preferably, the turbidity of the compositions according to the invention, measured at ambient temperature (25° C.) and atmospheric pressure, is less than 400 NTU units, more preferentially between 1 and 250 NTU units, even better still between 3 and 200 NTU units.

Preferably, the composition is free of cationic surfactant, of cationic polymer and/or of cationic silicone. The expression "free of cationic surfactant, of cationic polymer and/or of cationic silicone" is intended to mean that the composition does not comprise cationic surfactant, cationic polymer and/or cationic silicone, or that the total content of cationic surfactant, cationic polymer and cationic silicone is less than or equal to 0.1% by weight relative to the total weight of the composition.

Non-Ionic Surfactants

The composition according to the present invention comprises at least one non-ionic surfactant of formula (I):

$$R-O-(CH_2-CH_2-O)_n-H \quad (I)$$

in which:
R is a linear or branched $C_8$-$C_{40}$ alkenyl radical;
n is an integer ranging from 6 to 20.

Preferably, R represents a linear or branched $C_{12}$-$C_{30}$, more preferentially $C_{16}$-$C_{20}$, alkenyl radical.

Preferably, n represents an integer ranging from 8 to 12.

According to one preferred embodiment of the invention, R represents a linear or branched $C_{16}$-$C_{20}$ alkenyl radical; and/or n represents an integer ranging from 8 to 12.

According to another preferred embodiment of the invention, the composition comprises at least one non-ionic surfactant of formula (I), chosen from oleyl alcohol comprising 8 mol of ethylene oxide, oleyl alcohol comprising 10 mol of ethylene oxide, and oleyl alcohol comprising 12 mol of ethylene oxide.

According to one particularly preferred embodiment of the invention, the composition comprises oleyl alcohol comprising 10 mol of ethylene oxide (INCI name: Oleth-10).

Preferably, the total content of the non-ionic surfactant(s) of formula (I) present in the composition according to the invention is between 0.1% and 20% by weight, more preferentially between 1% and 15% by weight, even more preferentially between 2.5% and 10% by weight, relative to the total weight of the composition.

Water

The composition according to the present invention comprises water.

Preferably, the total water content is between 20% and 97% by weight, preferably between 30% and 95%, preferentially between 50% and 93% by weight and even better still between 65% and 90% by weight relative to the total weight of the composition.

According to one variant of the invention, the composition comprises a mixture of water and one or more cosmetically acceptable organic solvents chosen from $C_1$-$C_4$ alcohols, such as ethanol, isopropanol, tert-butanol or n-butanol; polyols such as glycerol, propylene glycol and polyethylene glycols, aromatic alcohols such as benzyl alcohol; and mixtures thereof.

According to this variant, the total content of organic solvent(s) is preferably between 0.1% and 40% by weight, more preferentially between 0.5% and 30% by weight, even more preferentially between 1 and 20% by weight, relative to the total weight of the composition.

The Propellants

The composition according to the present invention comprises one or more propellants.

The propellant(s) that may be used according to the invention are preferably chosen from liquefied gases such as dimethyl ether, chlorinated and/or fluorinated hydrocarbons such as trichlorofluoromethane, dichlorodifluoromethane, chlorodifluoromethane, 1,1,1,2-tetrafluoroethane, chloropentafluoroethane, 1-chloro-1,1-difluoroethane or 1,1-difluoroethane, or volatile hydrocarbons especially such as $C_3$-$C_5$ alkanes, for instance propane, isopropane, n-butane, isobutane or pentane; and mixtures thereof.

According to one preferred embodiment of the invention, the propellant(s) are chosen from volatile, optionally halogenated, hydrocarbons, for example n-butane, propane, isobutane, pentane and halogenated derivatives thereof; dimethyl ether; and mixtures thereof; more preferentially from dimethyl ether, $C_3$-$C_5$ alkanes, in particular propane, n-butane and isobutane, and mixtures thereof.

Preferably, the propellant(s) used are entirely dissolved or dispersed in the composition before the first use of the composition. The expression "entirely dissolved or dispersed in the composition" is intended to mean that the propellant(s) are totally dissolved or dispersed in the composition, or that the content of the propellant(s) not dissolved or not dispersed in the composition is less than 0.5% by weight relative to the total weight of the composition.

Preferably, the total content of the propellant(s) present in the composition is between 0.1% and 20% by weight, more preferentially between 0.5% and 15% by weight, and even more preferentially between 1% and 7% by weight, relative to the total weight of the composition.

The Fixing Polymers

The composition according to the present invention may optionally also comprise one or more fixing polymers.

For the purposes of the invention, the term "fixing polymer" is intended to mean any polymer that is capable, by application to the hair, of giving a shape to the head of hair or of holding an already acquired shape.

All the anionic, amphoteric and non-ionic fixing polymers and mixtures thereof used in the art may be used in the compositions according to the present application.

Preferably, the fixing polymer(s) according to the invention are chosen from non-ionic fixing polymers and anionic fixing polymers, and mixtures thereof.

More preferentially, the fixing polymer(s) are chosen from non-ionic fixing polymers.

The anionic fixing polymers generally used are polymers containing groups derived from carboxylic, sulfonic or phosphoric acid, and have a number-average molecular weight of between approximately 500 and 5 000 000.

The carboxylic groups are provided by unsaturated mono- or dicarboxylic acid monomers, such as those corresponding to formula (III):

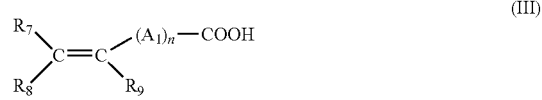

in which n is an integer from 0 to 10, $A_1$ denotes a methylene group, optionally connected to the carbon atom of the unsaturated group or to the adjacent methylene group when n is greater than 1, via a heteroatom, such as oxygen or sulfur, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group or a —$CH_2$—COOH, phenyl or benzyl group.

In the abovementioned formula, a lower alkyl group preferably denotes a group having 1 to 4 carbon atoms and in particular methyl and ethyl groups. The anionic fixing polymers containing carboxylic groups that are preferred according to the invention are:

A) copolymers of acrylic or methacrylic acid or salts thereof.

Mention may be made, among these polymers, of copolymers of acrylic or methacrylic acid with a monoethylenic monomer, such as ethylene, styrene, vinyl esters or acrylic or methacrylic acid esters, optionally grafted to a polyalkylene glycol, such as polyethylene glycol, and optionally crosslinked. Such polymers are described in particular in French patent No. 1 222 944 and German application No. 2330956, the copolymers of this type comprising an optionally N-alkylated and/or hydroxyalkylated acrylamide unit in their chain, as described in particular in the Luxembourgian patent applications Nos. 75370 and 75371. Mention may also be made of copolymers of acrylic acid and of $C_1$-$C_4$ alkyl methacrylate and terpolymers of vinylpyrrolidone, of acrylic acid and of $C_1$-$C_{20}$ alkyl methacrylate, for example lauryl methacrylate, such as that sold by ISP under the name Acrylidone® LM (INCI name: VP/acrylates/lauryl methacrylate copolymer), acrylic acid/ethyl acrylate/N-(t-butyl) acrylamide terpolymers, such as the products Ultrahold® Strong and Ultrahold® 8 sold by BASF (INCI name: Acrylates/t-butylacrylamide copolymer), methacrylic acid/ethyl acrylate/tert-butyl acrylate terpolymers, such as the products sold under the names Luvimer® 100 P or Luvimer® PRO 55 by BASF (INCI name: Acrylates copolymer), copolymers of methacrylic acid and of ethyl acrylate, such as the products sold under the names Luvimer® MAE or Luviflex® Soft by BASF (INCI name: Acrylates copolymer), acrylic acid/butyl acrylate/methyl methacrylate terpolymers, such as the product sold under the name Balance® CR by AkzoNobel (INCI name: Acrylates copolymer), or the copolymers of methacrylic acid and of methyl methacrylate sold under the name Eudragit® L 100 by Rohm Pharma (INCI name: Acrylates copolymer). Mention may also be made of branched block polymers containing (meth)acrylic acid monomers, such as the product sold under the name Fixate® G-100L by the company Lubrizol (INCI name AMP-acrylates/allyl methacrylate copolymer);

B) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid. Such polymers are described, inter alia, in French patents Nos. 1 222 944, 1 580 545, 2 265 782, 2 265 781, 1 564 110 and 2 439 798. Commercial products which fall into this category are the products Resyn® 28-2930 and 28-1310 sold by the company AkzoNobel (INCI names VA/crotonates/vinyl decanoate copolymer and VA/crotonates copolymer, respectively). Mention may also be made of the products Luviset® CA 66 sold by the company BASF, Aristoflex® A60 sold by the company Clariant (INCI name VA/crotonates copolymer) and Mexomere® PW or PAM sold by the company Chimex (INCI name VA/vinyl butyl benzoate/crotonates copolymer);

C) copolymers of $C_4$-$C_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, or acrylic acid and its esters, the anhydride functions of these copolymers optionally being monoesterified or monoamidated. Such polymers are described, in particular, in U.S. Pat. Nos. 2,047,398, 2,723,248 and 2,102,113, and patent GB 839 805. Commercial products are in particular those sold under the names Gantrez® AN or ES by the company ISP, such as Gantrez® ES 225 (INCI name Ethyl ester of PVM/MA copolymer) or Gantrez® ES 425L (INCI name Butyl ester of PVM/MA copolymer);

copolymers comprising (i) one or more maleic, citraconic or itaconic anhydride units and (ii) one or more monomers chosen from allyl or methallyl esters, optionally comprising one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

These polymers are described, for example, in patents FR 2 350 384 and FR 2 357 241;

D) polyacrylamides comprising carboxylate groups.

The fixing polymers comprising units derived from sulfonic acid can be chosen from:

A') homopolymers and copolymers comprising vinylsulfonic, styrenesulfonic, naphthalenesulfonic or acrylamidoalkylsulfonic units.

These polymers may be chosen especially from:

polyvinylsulfonic acid salts with a molecular weight of between 1,000 and 100 000 approximately, and also the copolymers with an unsaturated comonomer such as acrylic or methacrylic acids and esters thereof, and also acrylamide or derivatives thereof, vinyl ethers and vinylpyrrolidone;

polystyrenesulfonic acid salts such as the sodium salts that are sold for example under the name Flexan® II by AkzoNobel (INCI name Sodium polystyrene sulfonate). These compounds are described in patent FR 2198719;

polyacrylamidosulfonic acid salts, such as those mentioned in U.S. Pat. No. 4,128,631, and more particularly the polyacrylamidoethylpropanesulfonic acid sold under the name Rheocare® HSP-1180 by Cognis (INCI name polyacrylamidomethylpropane sulfonic acid);

B') sulfonic polyesters, these polymers being advantageously obtained by polycondensation of at least one dicarboxylic acid, of at least one diol or of a mixture of diol and of diamine, and of at least one difunctional monomer comprising a sulfonic function. Among these polymers, mention may be made of:

linear sulfonic polyesters such as those described in patent applications U.S. Pat. Nos. 3,734,874, 3,779,993, 4,119,680, 4,300,580, 4,973,656, 5,660,816, 5,662,893 and 5,674,479. Such polymers are, for example, the products Eastman® AQ38S Polymer, Eastman® AQ55S Polymer and Eastman® AQ48 Ultra Polymer sold by the company Eastman Chemical (name Polyester-5) which are copolymers obtained from diethylene glycol, from 1,4-cyclohexanedimethanol, from isophthalic acid and from sulfoisophthalic acid salt;

branched sulfonic polyesters such as those described in patent applications WO 95/18191, WO 97/08261 and WO 97/20899. Such compounds are for example the products Eastman® AQ10D Polymer (name Polyester-13) or Eastman® AQ1350 Polymer provided by the company Eastman Chemical (name Polyester-13).

According to the invention, the anionic fixing polymers are preferably chosen from copolymers of acrylic acid, such as the acrylic acid/ethyl acrylate/N-tert-butylacrylamide terpolymers sold in particular under the name Ultrahold® Strong by the company BASF, copolymers derived from crotonic acid, such as vinyl acetate/vinyl tert-butylbenzoate/crotonic acid terpolymers and the crotonic acid/vinyl acetate/vinyl neododecanoate terpolymers sold in particular under the name Resyn 28-2930 by the company AkzoNobel, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the names Gantrez® \ES 425L or ES 225 by the company ISP, the copolymers of methacrylic acid and of ethyl acrylate sold under the name Luvimer® MAE by the company BASF, and the vinyl acetate/crotonic acid copolymers sold under the name Luviset® CA 66 by the company BASF, and the vinyl acetate/crotonic acid copolymers grafted with polyethylene glycol sold under the name Aristoflex® A60 by the company Clariant, the vinylpyrrolidone/acrylic acid/lauryl methacrylate terpolymers sold under the name Acrylidone® LM by the company ISP, the polymer sold under the name Fixate® G-100L by the company Lubrizol, the vinyl acetate/crotonic acid/vinyl p-tert-butylbenzoate copolymers sold under the names Mexomere® PW or PAM by the company Chimex.

Preferably, when they are present, the composition according to the invention comprises the anionic fixing polymer(s) in an amount ranging from 0.1% to 20% by weight, preferentially from 0.2% to 15% by weight, and even more preferentially from 0.3% to 10% by weight, relative to the total weight of the composition.

The amphoteric fixing polymers which can be used in accordance with the invention can be chosen from polymers comprising B and C units randomly distributed in the polymer chain, where B denotes a unit deriving from a monomer comprising at least one basic nitrogen atom and C denotes a unit deriving from an acidic monomer comprising one or more carboxylic or sulfonic groups or else B and C can denote groups deriving from zwitterionic carboxybetaine or sulfobetaine monomers;

B and C may also denote a cationic polymer chain comprising primary, secondary, tertiary or quaternary amine groups, in which at least one of the amine groups bears a carboxylic or sulfonic group connected via a hydrocarbon-based group or alternatively B and C form part of a chain of a polymer comprising an α,β-dicarboxylic ethylene unit in which one of the carboxylic groups has been made to react with a polyamine comprising one or more primary or secondary amine groups.

The amphoteric fixing polymers corresponding to the definition given above which are more particularly preferred are chosen from the following polymers:

(1) copolymers having acidic vinyl units and basic vinyl units, such as those resulting from the copolymerization of a monomer derived from a vinyl compound bearing a carboxylic group such as, more particularly, acrylic acid, methacrylic acid, maleic acid, alpha-chloroacrylic acid, and a basic monomer derived from a substituted vinyl compound containing at least one basic atom, such as, more particularly, dialkylaminoalkyl methacrylate and acrylate, dialkylaminoalkylmethacrylamides and acrylamides. Such compounds are described in U.S. Pat. No. 3,836,537;

(2) polymers comprising units deriving:
  a) from at least one monomer chosen from acrylamides and methacrylamides substituted on the nitrogen atom with an alkyl group,
  b) from at least one acidic comonomer containing one or more reactive carboxylic groups, and
  c) at least one basic comonomer such as esters with primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are more particularly chosen from acrylic acid, methacrylic acid, crotonic acid, itaconic acid, maleic acid and fumaric acid and alkyl monoesters, containing 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers of which the INCI name is Octylacrylamide/acrylates/butylaminoethyl methacrylate copolymer, such as the products sold under the names Amphomer®, Amphomer® LV71 or Balance® 47 by the company AkzoNobel, are particularly used;

(3) partially or completely acylated and crosslinked polyaminoamides deriving from polyaminoamides of general formula (IV):

 (IV)

in which $R_{10}$ represents a divalent group derived from a saturated dicarboxylic acid, from an aliphatic mono- or dicarboxylic acid comprising an ethylenic double bond, from an ester of a lower alkanol having from 1 to 6 carbon atoms of these acids, or from a group deriving from the addition of any one of said acids with a bisprimary or bissecondary amine, and Z denotes a group deriving from a bisprimary, mono- or bissecondary polyalkylenepolyamine and preferably represents:
  a) in proportions of from 60 mol % to 100 mol %, the group (V)

 (V)

in which x=2 and p=2 or 3, or else x=3 and p=2, this group deriving from diethylenetriamine, from triethylenetetramine or from dipropylenetriamine;
  b) in proportions of from 0 to 40 mol %, the group (V) above in which x=2 and p=1 and which is derived from ethylenediamine, or the group deriving from piperazine:

c) in the proportions of from 0 mol % to 20 mol %, the group —NH—$(CH_2)_6$—NH— deriving from hexamethylenediamine, these polyaminoamides being crosslinked by addition reaction of a bifunctional crosslinking agent chosen from epihalohydrins, diepoxides, dianhydrides or bisunsaturated derivatives, by means of from 0.025 to 0.35 mol of crosslinking agent per amine group of the polyaminoamide, and acylated by action of acrylic acid, chloroacetic acid or an alkane sultone or salts thereof.

The saturated carboxylic acids are preferably chosen from acids containing 6 to 10 carbon atoms, such as adipic acid, 2,2,4-trimethyladipic acid, 2,4,4-trimethyladipic acid and terephthalic acid, and acids bearing an ethylenic double bond, for instance acrylic, methacrylic and itaconic acids.

The alkane sultones used in the acylation are preferably propane sultone or butane sultone; the salts of the acylating agents are preferably the sodium or potassium salts.

(4) Polymers comprising zwitterionic units of formula (VI):

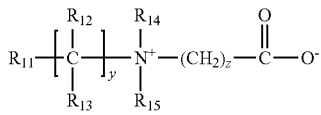  (VI)

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or a methyl, ethyl or propyl group, and $R_{14}$ and $R_{15}$ represent a hydrogen atom or an alkyl group such that the sum of the carbon atoms in $R_{14}$ and $R_{15}$ does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

Mention may be made, by way of example, of methyl methacrylate/methyl dimethylcarboxymethylammonioethyl methacrylate copolymers, such as the product sold under the name Diaformer Z-301N or Z-301W by the company Clariant (INCI name Acrylates copolymer);

(5) polymers derived from chitosan comprising monomer units corresponding to the following formulae (D), (E) and (F):

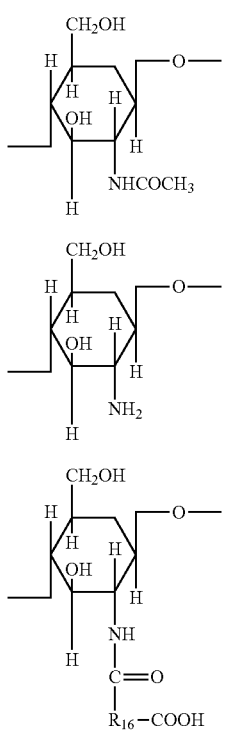

the unit (D) being present in proportions of between 0 and 30%, the unit (E) in proportions of between 5% and 50% and the unit (F) in proportions of between 30% and 90%, it being understood that, in this unit (F), $R_{16}$ represents a group of formula (VII):

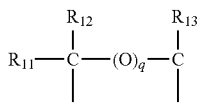  (VII)

in which if q=0, $R_{11}$, $R_{12}$ and $R_{13}$, which may be identical or different, each represent a hydrogen atom, a methyl, hydroxyl, acetoxy or amino residue, a monoalkylamine residue or a dialkylamine residue that are optionally interrupted with one or more nitrogen atoms and/or optionally substituted with one or more amine, hydroxyl, carboxyl, alkylthio or sulfonic groups, an alkylthio residue in which the alkyl group bears an amino residue, at least one of the groups $R_{11}$, $R_{12}$ and $R_{13}$ being, in this case, a hydrogen atom;

or, if q=1, $R_{11}$, $R_{12}$ and $R_{13}$ each represent a hydrogen atom, and also the salts formed by these compounds with bases or acids;

(6) polymers containing units conforming to the general formula (VIII) are described, for example, in French patent FR 1 400 366:

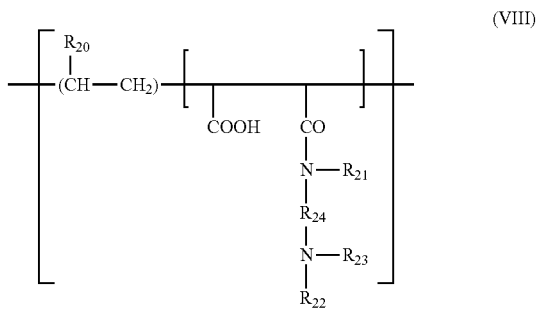  (VIII)

in which $R_{20}$ represents a hydrogen atom or a $CH_3O$—, $CH_3CH_2O$— or phenyl group, $R_{21}$ denotes a hydrogen atom or a lower alkyl group, such as methyl or ethyl, $R_{22}$ denotes a hydrogen atom or a lower $C_1$-$C_6$ alkyl group, such as methyl or ethyl, and $R_{23}$ denotes a lower $C_1$-$C_6$ alkyl group, such as methyl or ethyl, or a group corresponding to the formula: —$R_{24}$—N($R_{22}$)$_2$, with $R_{24}$ representing a —$CH_2$—$CH_2$—, —$CH_2$—$CH_2$—$CH_2$—, or —$CH_2$—$CH(CH_3)$— group and $R_{22}$ having the meanings given above;

(7) polymers derived from the N-carboxyalkylation of chitosan, such as N-(carboxymethyl)chitosan or N-(carboxybutyl)chitosan, such as, for example, the product sold under the name Chitoglycan by Sinerga SPA (INCI name: Carboxymethyl chitosan);

(8) amphoteric polymers of the -D-X-D-X type chosen from:
a) polymers obtained by the action of chloroacetic acid or sodium chloroacetate on compounds comprising at least one unit of formula (IX):

-D-X-D-X-D-  (IX)

in which D denotes a group

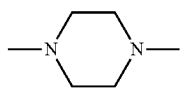

and X denotes the symbol E or E', where E or E', which may be identical or different, denote a divalent group that is an alkylene group with a straight or branched chain containing up to 7 carbon atoms in the main chain, which is unsubstituted or substituted with hydroxyl groups and which may comprise, in addition to oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula (X):

 (X)

in which D denotes a group

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate;

(9) $(C_1-C_5)$alkyl vinyl ether/maleic anhydride copolymers partially modified by semiamidation with an N,N-dialkylaminoalkylamine, such as N,N-dimethylaminopropylamine, or by semiesterification with an N,N-dialkylaminoalkanol. These copolymers may also comprise other vinyl comonomers, such as vinylcaprolactam.

Mention will be made, among the abovementioned most particularly preferred amphoteric fixing polymers according to the invention, of those of family (3), such as the copolymers of which the INCI name is Octylacrylamide/acrylates/butylaminoethyl methacrylate copolymer, such as the products sold under the names Amphomer®, Amphomer® LV 71 or Balance® 47 by the company AkzoNobel, and those of family (4), such as methyl methacrylate/methyl dimethylcarboxymethylammonioethyl methacrylate copolymers, sold, for example, under the name Diaformer Z-301N or Z-301W by the company Clariant.

Preferably, when they are present, the composition according to the invention comprises the amphoteric fixing polymer(s) in an amount ranging from 0.1% to 20% by weight, preferentially from 0.2% to 15% by weight, and even more preferentially from 0.3% to 10% by weight, relative to the total weight of the composition.

The non-ionic fixing polymers that may be used according to the present invention are chosen, for example, from:
polyalkyloxazolines;
vinyl acetate homopolymers,
vinyl acetate copolymers, such as, for example, copolymers of vinyl acetate and of acrylic ester, copolymers of vinyl acetate and of ethylene, or copolymers of vinyl acetate and of maleic ester, for example of dibutyl maleate;

acrylic ester homopolymers and copolymers, such as, for example, copolymers of alkyl acrylates and of alkyl methacrylates, such as the products provided by Rohm GmbH under the name Eudragit® NE 30 D (INCI name: Acrylates copolymer);
copolymers of acrylonitrile and of a non-ionic monomer chosen, for example, from butadiene and alkyl (meth)acrylates;
styrene homopolymers;
styrene copolymers, such as, for example, copolymers of styrene, of alkyl acrylate and of alkyl methacrylate; copolymers of styrene and of butadiene; or copolymers of styrene, of butadiene and of vinylpyridine;
polyamides;
vinyllactam homopolymers, such as the vinylpyrrolidone homopolymers sold, for example, under the names Luviskol® K30 powder by the company BASF or PVP K30L or K60 solution or K90 by the company ISP, or such as the polyvinylcaprolactam sold under the name Luviskol® Plus by the company BASF (INCI name PVP);
vinyllactam copolymers, such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVP/VA® S630L, E735, E635 and W735 by the company ISP, Luviskol® VA 73, VA 64 and VA 37 by the company BASF (INCI name VP/VA copolymer); and vinylpyrrolidone/methacrylamide/vinylimidazole terpolymers, for instance the product sold under the name Luviset® Clear by the company BASF (INCI name VP/methacrylamide/vinyl imidazole copolymer).

The alkyl groups of the non-ionic polymers mentioned above preferably contain from 1 to 6 carbon atoms.

Preferably, when they are present, the composition according to the invention comprises the non-ionic fixing polymer(s) in an amount ranging from 0.1% to 20% by weight, preferentially from 0.2% to 15% by weight, and even more preferentially from 0.3% to 10% by weight, relative to the total weight of the composition.

Use may also be made, according to the invention, of fixing polymers of grafted silicone type comprising a polysiloxane portion and a portion composed of a non-silicone organic chain, one of the two portions constituting the main chain of the polymer and the other being grafted to said main chain.

These polymers are described, for example, in the patent applications EP-A-0 412 704, EP-A-0 412 707, EP-A-0 640 105 and WO 95/00578, EP-A-0 582 152 and WO 93/23009, and the patents U.S. Pat. Nos. 4,693,935, 4,728,571 and 4,972,037.

These polymers can be amphoteric, anionic or non-ionic and they are preferably anionic or non-ionic.

Such polymers are, for example, copolymers that may be obtained by free radical polymerization from the monomer mixture formed from:
a) 50% to 90% by weight of tert-butyl acrylate,
b) 0% to 40% by weight of acrylic acid,
c) 5% to 40% by weight of a silicone macromer of formula:

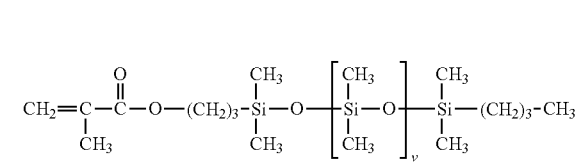

where v is a number ranging from 5 to 700, the percentages by weight being calculated relative to the total weight of the monomers.

Other examples of grafted silicone polymers are in particular polydimethylsiloxanes (PDMSs) to which mixed polymer units of the poly((meth)acrylic acid) type and of the poly(alkyl (meth)acrylate) type are grafted via a thiopropylene-type connecting link and polydimethylsiloxanes (PDMSs) to which polymer units of the poly(isobutyl (meth) acrylate) type are grafted via a thiopropylene-type connecting link.

Grafted silicone polymers are, for example, sold under the names Silicone Plus Polymer® VS80 and VA70 by 3M (INCI names Polysilicone-8 and Polysilicone-7 respectively).

Another type of silicone fixing polymer that may be mentioned is the product Luviflex® Silk sold by BASF (INCI name PEG/PPG-25/25 dimethicone/acrylates copolymer).

Preferably, when they are present, the composition according to the invention comprises the fixing polymer(s) of grafted silicone type in an amount ranging from 0.1% to 20% by weight, preferentially from 0.2% to 15% by weight, and even more preferentially from 0.3% to 10% by weight, relative to the total weight of the composition.

Functionalized or non-functionalized, silicone or non-silicone, non-ionic, anionic or amphoteric polyurethanes or mixtures thereof may also be used as fixing polymers.

The polyurethanes particularly targeted by the present invention are those described in the patent applications EP 0 751 162, EP 0 637 600, EP 0 648 485 and FR 2 743 297, of which the applicant company is the proprietor, and also in the patent applications EP 0 656 021 and WO 94/03510 of BASF and EP 0 619 111 of National Starch.

Mention may be made, as polyurethanes particularly suitable in the present invention, of the products sold under the names Luviset PUR® and Luviset® Si PUR by the company BASF (INCI names Polyurethane-1 and Polyurethane-6 respectively).

Preferably, when they are present, the composition according to the invention comprises the polyurethane(s) in an amount ranging from 0.1% to 20% by weight, preferentially from 0.2% to 15% by weight, and even more preferentially from 0.3% to 10% by weight, relative to the total weight of the composition.

Preferably, the composition according to the invention also comprises one or more fixing polymers chosen from non-ionic fixing polymers, anionic fixing polymers, and mixtures thereof; preferentially chosen from non-ionic fixing polymers; more preferentially chosen from vinyllactam homopolymers such as homopolymers of vinylpyrrolidone and polyvinylcaprolactam, and vinyllactam copolymers such as poly(vinylpyrrolidone/vinyllactam) copolymers and poly(vinylpyrrolidone/vinyl acetate) copolymers; and mixtures thereof.

Preferably, when they are present, the composition according to the invention comprises the fixing polymer(s) in a total amount ranging from 0.1% to 20% by weight, preferentially from 0.2% to 15% by weight, and even more preferentially from 0.3% to 10% by weight, relative to the total weight of the composition.

The Oils

The composition according to the present invention may optionally also comprise one or more oils.

The term "oil" is intended to mean any fatty substance that is in liquid form at ambient temperature (25° C.) and at atmospheric pressure.

The term "fatty substance" is intended to mean an organic compound that is insoluble in water at ambient temperature (25° C.) and at atmospheric pressure ($1.013 \times 10^5$ Pa) (solubility of less than 5% by weight, preferably less than 1% by weight and even more preferentially less than 0.1% by weight). They bear in their structure at least one hydrocarbon-based chain comprising at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The oil(s) optionally present in the composition according to the invention may be volatile or non-volatile.

The volatile or non-volatile oils may be hydrocarbon-based oils, especially of animal or plant origin, synthetic oils, silicone oils or fluoro oils, and/or mixtures thereof.

For the purposes of the present invention, the term "silicone oil" is intended to mean an oil comprising at least one silicon atom, and especially at least one Si—O group.

The term "hydrocarbon-based oil" is intended to mean an oil mainly containing hydrogen and carbon atoms and possibly oxygen, nitrogen, sulfur and/or phosphorus atoms. A hydrocarbon-based oil does not comprise any silicon atoms.

The oil(s) present in the composition according to the invention may be non-volatile.

For the purposes of the present invention, the term "non-volatile oil" is intended to mean an oil with a vapour pressure of less than 0.13 Pa (0.01 mmHg).

The non-volatile oils may be chosen especially from hydrocarbon-based oils, which may be fluorinated, and/or non-volatile silicone oils.

As non-volatile hydrocarbon-based oils that are suitable for use in the invention, mention may be made especially of:
hydrocarbon-based oils of animal origin,
hydrocarbon-based oils of plant origin such as phytostearyl esters, such as phytostearyl oleate, phytostearyl isostearate and lauroyl/octyldodecyl/phytostearyl glutanate, for example sold under the name Eldew PS203 by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, sweet almond oil, argan oil, avocado oil, groundnut oil, *camellia* oil, safflower oil, beauty-leaf oil, rapeseed oil, copra oil, coriander oil, marrow oil, wheatgerm oil, jojoba oil or liquid jojoba wax, linseed oil, macadamia oil, corn germ oil, hazelnut oil, walnut oil, *vernonia* oil, apricot kernel oil, olive oil, evening primrose oil, palm oil, passion flower oil, grapeseed oil, rose oil, castor oil, rye oil, sesame oil, rice bran oil, camelina oil, soybean oil, sunflower oil, pracaxi oil, babassu oil, mongongo oil, manila oil, arara oil, shea butter oil, Brazil nut oil; or alternatively caprylic/capric acid triglycerides, for instance those sold by the company Stéarineries Dubois or those sold under the names Miglyol 810®, 812® and 818® by the company Dynamit Nobel, and the refined plant perhydrosqualene sold under the name Fitoderm by the company Cognis; the plant squalene sold, for example, under the name Squalive by the company Biosynthis;
hydrocarbon-based oils of mineral or synthetic origin, for instance:

(a) synthetic ethers containing from 10 to 40 carbon atoms;
(b) linear or branched hydrocarbons of mineral or synthetic origin, such as petroleum jelly, liquid paraffin or derivatives thereof, polydecenes, hydrogenated polyisobutene such as parleam, squalane, and mixtures thereof, and in particular hydrogenated polyisobutylene and liquid paraffin;
(c) synthetic esters, for instance oils of formula $R_1COOR_2$ in which $R_1$ represents a linear or branched fatty acid residue containing from 1 to 40 carbon atoms and $R_2$ represents a hydrocarbon-based chain that is especially branched, containing from 1 to 40 carbon atoms provided that $R_1+R_2 \geq 10$.

The esters may be chosen especially from especially fatty acid esters, for instance:
cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;
polyol esters and pentaerythritol esters, for instance dipentaerythrityl tetrahydroxystearate/tetraisostearate;
esters of diol dimers and of diacid dimers, such as Lusplan DD-DA5® and Lusplan DD-DA7® sold by the company Nippon Fine Chemical and described in patent application FR 03 02809;
(d) fatty alcohols that are liquid at ambient temperature, bearing a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecyl pentadecanol;
(e) non-salified higher fatty acids such as oleic acid, linoleic acid and linolenic acid, and mixtures thereof; and
(f) dialkyl carbonates, the two alkyl chains possibly being identical or different, such as the dicaprylyl carbonate sold under the name Cetiol CC® by Cognis;
(g) and mixtures thereof.

The non-volatile silicone oils are chosen, for example, from non-volatile polydimethylsiloxanes (PDMSs), polydimethylsiloxanes comprising alkyl or alkoxy groups that are pendent and/or at the ends of a silicone chain, these groups each having from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof.

The non-volatile oils may be chosen from mixtures of hydrocarbon-based and silicone non-volatile oils.

The oil(s) present in the composition according to the invention may also be volatile.

For the purposes of the present invention, "volatile oil" is intended to mean an oil (or non-aqueous medium) that is capable of evaporating on contact with the skin in less than one hour, at ambient temperature and at atmospheric pressure. The volatile oil is a volatile cosmetic oil, which is liquid at ambient temperature, especially having a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon-based oils may be chosen from hydrocarbon-based oils containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile fluoro oils such as nonafluoromethoxybutane or perfluoromethylcyclopentane, and mixtures thereof, may also be used.

Volatile oils that may also be used include volatile silicones, for instance volatile linear or cyclic silicone oils, especially those with a viscosity ≤8 centistokes ($8\times10^{-6}$ $m^2/s$), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with a viscosity of 5 and cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

It is also possible to use a mixture of hydrocarbon-based and silicone volatile oils.

Preferably, the oil(s) are chosen from $C_6$-$C_{16}$ alkanes, linear or branched hydrocarbons of mineral or synthetic origin containing more than 16 carbon atoms, non-silicone oils of animal origin, oils of plant origin, fluoro oils, liquid fatty alcohols, liquid fatty esters, non-salified liquid fatty acids, silicone oils, and mixtures of these compounds.

For the purposes of the present invention, the term "fatty alcohol, ester or acid" is intended to mean an alcohol, ester or acid comprising a linear or branched, saturated or unsaturated alkyl chain, comprising at least 8 carbon atoms, preferably from 8 to 30 carbon atoms and more preferentially from 12 to 24 carbon atoms.

Particularly preferably, the oil(s) are chosen from $C_6$-$C_{16}$ alkanes, linear or branched hydrocarbons of mineral or synthetic origin containing more than 16 carbon atoms, liquid fatty alcohols, liquid fatty esters, oils of plant origin, especially hydrocarbon-based oils of plant origin, and mixtures of these compounds.

Most particularly preferably, the oil(s) are chosen from $C_6$-$C_{16}$ alkanes, linear or branched hydrocarbons of mineral or synthetic origin containing more than 16 carbon atoms, liquid fatty alcohols, oils of plant origin, especially hydrocarbon-based oils of plant origin, and mixtures of these compounds.

According to one preferred embodiment of the invention, the composition comprises one or more oils chosen from $C_6$-$C_{16}$ alkanes, linear or branched hydrocarbons of mineral or synthetic origin containing more than 16 carbon atoms, non-silicone oils of animal origin, oils of plant origin, fluoro oils, liquid fatty alcohols, liquid fatty esters, non-salified liquid fatty acids, silicone oils, and mixtures of these compounds, preferably chosen from $C_6$-$C_{16}$ alkanes, linear or branched hydrocarbons of mineral or synthetic origin containing more than 16 carbon atoms, liquid fatty alcohols, liquid fatty esters, oils of plant origin, especially hydrocarbon-based oils of plant origin, and mixtures of these compounds, and more preferentially chosen from $C_6$-$C_{16}$ alkanes, linear or branched hydrocarbons of mineral or synthetic origin containing more than 16 carbon atoms, liquid fatty alcohols, oils of plant origin, especially hydrocarbon-based oils of plant origin, and mixtures of these compounds.

Preferably, when they are present, the composition according to the invention comprises the oil(s) in a total content ranging from 1% to 30% by weight, preferentially from 3% to 25% by weight, and even more preferentially from 5% to 20% by weight, relative to the total weight of the composition.

The Additional Surfactants

The composition according to the present invention can optionally also comprise one or more additional surfactants chosen from anionic surfactants, non-ionic surfactants other than the non-ionic surfactants of formula (I) as previously described, and mixtures thereof.

Preferably, the additional surfactant(s) according to the invention are chosen from non-ionic surfactants other than the non-ionic surfactants of formula (I) previously described.

The anionic surfactants that may be present in the composition according to the invention may be chosen especially from anionic derivatives of proteins of plant origin or of silk proteins, phosphates and alkyl phosphates, carboxylic acids and carboxylates, sulfosuccinates, amino acid derivatives, alkyl sulfates, alkyl ether sulfates, sulfonates, isethionates, taurates, alkyl sulfoacetates, polypeptides, anionic derivatives of alkyl polyglucoside, soaps (fatty acid salts), and mixtures thereof.

a) Anionic derivatives of proteins of plant origin are protein hydrolysates bearing a hydrophobic group, it being possible for said hydrophobic group to be naturally present in the protein or to be added by reaction of the protein and/or of the protein hydrolysate with a hydrophobic compound. The proteins are of plant origin or are derived from silk, and the hydrophobic group may in particular be a fatty chain, for example an alkyl chain comprising from 10 to 22 carbon atoms. As anionic derivatives of proteins of plant origin, mention may more particularly be made of apple, wheat, soybean or oat protein hydrolysates comprising an alkyl chain containing from 10 to 22 carbon atoms, and salts thereof. The alkyl chain may especially be a lauryl chain and the salt may be a sodium, potassium and/or ammonium salt.

Thus, as protein hydrolysates bearing a hydrophobic group, mention may be made, for example, of salts of protein hydrolysates where the protein is a silk protein modified with lauric acid, such as the product sold under the name Kawa Silk by Kawaken; salts of protein hydrolysates where the protein is a wheat protein modified with lauric acid, such as the potassium salt sold under the name Aminofoam W OR by Croda (CTFA name: potassium lauroyl wheat amino acids) and the sodium salt sold under the name Proteol LW 30 by the company SEPPIC (CTFA name: sodium lauroyl wheat amino acids); salts of protein hydrolysates where the protein is an oat protein comprising an alkyl chain containing from 10 to 22 carbon atoms and more especially salts of protein hydrolysates where the protein is an oat protein modified with lauric acid, such as the sodium salt sold under the name Proteol OAT (30% aqueous solution) by the company SEPPIC (CTFA name: sodium lauroyl oat amino acids); or salts of apple protein hydrolysates comprising an alkyl chain containing from 10 to 22 carbon atoms, such as the sodium salt sold under the name Proteol APL (30% aqueous glycol solution) by the company SEPPIC (CTFA name: Sodium Cocoyl Apple amino acids). Mention may also be made of the mixture of lauroyl amino acids (aspartic, glutamic, glycine, alanine) neutralized with sodium N-methylglycinate sold under the name Proteol SAV 50 S by the company SEPPIC (CTFA name: Sodium Cocoyl amino acids).

b) Examples of phosphates and alkyl phosphates that may be mentioned include monoalkyl phosphates and dialkyl phosphates, such as the lauryl monophosphate sold under the name MAP 20® by the company Kao Chemicals, the potassium salt of dodecylphosphoric acid, a mixture of monoester and diester (predominantly diester) sold under the name Crafol AP-310 by the company Cognis, the mixture of octylphosphoric acid monoester and diester sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium or triethanolamine salt of mono(C12-C13)alkyl phosphate sold under the references Arlatone MAP 230K-40® and Arlatone MAP 230T-60® by the company Uniqema, the potassium lauryl phosphate sold under the name Dermalcare MAP XC-99/09® by the company Rhodia Chimie, and the potassium cetyl phosphate sold under the name Arlatone MAP 160K by the company Uniqema.

c) As carboxylic acids and carboxylates, mention may for example be made of amide ether carboxylates (AECs), such as sodium laurylamide ether carboxylate (3 EO), sold under the name Akpyo Foam 30® by the company Kao Chemicals, polyoxyethylenated carboxylic acid salts, such as oxyethylenated (6 EO) sodium lauryl ether carboxylate (C12-14-16 65/25/10) sold under the name Akpyo Soft 45 NV® by the company Kao Chemicals, polyoxyethylenated and carboxymethylated fatty acids of olive oil origin, sold under the name Olivem 400® by the company Biologia e Tecnologia, oxyethylenated (6 EO) sodium tridecyl ether carboxylate sold under the name Nikkol ECTD-6NEX® by the company Nikkol, fatty acids having a $C_6$ to $C_{22}$ alkyl chain, such as stearic acid, and fatty acid salts (soaps) having a $C_6$ to $C_{22}$ alkyl chain, neutralized with an organic or mineral base such as potassium hydroxide, sodium hydroxide, triethanolamine, N-methyl glucamine, lysine and arginine.

d) Amino acid derivatives that may especially be mentioned include alkaline salts of amino acids, such as:
  sarcosinates, for instance sodium cocoyl sarcosinate, the sodium lauroyl sarcosinate sold under the name Sarkosyl NL 97® by the company Ciba or sold under the name Oramix L 30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol;
  alaninates, for instance sodium N-lauroyl N-methyl amidopropionate sold under the name Sodium Nikkol Alaninate LN 30® by the company Nikkol, or sold under the name Alanone ALE® by the company Kawaken, and triethanolamine N-lauroyl N-methyl alanine sold under the name Alanone Alta® by the company Kawaken;

glutamates, for instance triethanolamine monococoyl glutamate sold under the name Acylglutamate CT-12® by the company Ajinomoto, triethanolamine lauroyl glutamate sold under the name Acylglutamate LT-12® by the company Ajinomoto, aspartates, for instance the mixture of triethanolamine N-lauroyl aspartate/triethanolamine N-myristoyl aspartate sold under the name Asparack® by the company Mitsubishi;

glycine derivatives (glycinates), for instance the sodium N-cocoyl glycinate sold under the names Amilite GCS-12® and Amilite GCK 12 by the company Ajinomoto;

citrates, such as the oxyethylenated (9 mol) citric monoester of cocoyl alcohols sold under the name Witconol EC 1129 by the company Goldschmidt, and galacturonates such as sodium dodecyl D-galactoside uronate sold by the company Soliance.

e) Examples of sulfosuccinates that may be mentioned include the oxyethylenated (3 EO) lauryl alcohol monosulfosuccinate (70/30 C12/C14) sold under the names Setacin 103 Special® and Rewopol SB-FA 30 K 4® by the company Witco, the disodium salt of a hemisulfosuccinate of C12-C14 alcohols, sold under the name Setacin F Special Paste® by the company Zschimmer Schwarz, the oxyethylenated (2 EO) disodium oleamidosulfosuccinate sold under the name Standapol SH 135® by the company Cognis, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco. Polydimethylsiloxane sulfosuccinates may also be used, such as the disodium PEG-12 dimethicone sulfosuccinate sold under the name Mackanate-DC30 by the company MacIntyre.

f) Examples of alkyl sulfates that may be mentioned include triethanolamine lauryl sulfate (CTFA name: TEA lauryl sulfate), such as the product sold by Huntsman under the name Empicol TL40 FL or the product sold by Cognis under the name Texapon T42, which products are at 40% in aqueous solution. Mention may also be made of ammonium lauryl sulfate (CTFA name: ammonium lauryl sulfate), such as the product sold by Huntsman under the name Empicol AL 30FL, which is at 30% in aqueous solution.

g) Examples of alkyl ether sulfates that may be mentioned include sodium lauryl ether sulfate (CTFA name: sodium laureth sulfate), such as the product sold under the names Texapon N40 and Texapon AOS 225 UP by the company Cognis, or ammonium lauryl ether sulfate (CTFA name: ammonium laureth sulfate), such as the product sold under the name Standapol EA-2 by the company Cognis.

h) Examples of sulfonates that may be mentioned include α-olefinsulfonates, such as the sodium α-olefinsulfonate (C14-C16), sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, secondary sodium olefinsulfonate, sold under the name Hostapur SAS 30® by the company Clariant; or linear alkylarylsulfonates, such as sodium xylenesulfonate, sold under the names Manrosol SXS30®, Manrosol SXS40® and Manrosol SXS93® by the company Manro.

i) Isethionates that may be mentioned include ($C_8$-$C_{18}$) acylisethionates, for instance sodium cocoyl isethionate, such as the product sold under the name Jordapon CI P® by the company Jordan.

j) Taurates that may be mentioned include the salts (in particular sodium salt) of palm kernel oil methyltaurate sold under the name Hostapon CT Paste® by the company Clariant; N—(C8-C18)acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

k) The anionic derivatives of ($C_8$-$C_{18}$)alkyl polyglucosides may especially be citrates, tartrates, sulfosuccinates, carbonates and ethers of glycerol obtained from alkyl polyglucosides. Mention may be made, for example, of the sodium salt of cocoyl polyglucoside (1,4) tartaric ester, sold under the name Eucarol AGE-ET® by the company Cesalpinia, the disodium salt of cocoyl polyglucoside (1,4) sulfosuccinic ester, sold under the name Essai 512 MP® by the company SEPPIC, or the sodium salt of cocoyl polyglucoside (1,4) citric ester, sold under the name Eucarol AGE-EC® by the company Cesalpinia.

l) The soaps are obtained from a fatty acid which is partially or completely saponified (neutralized) with a basic agent. These are alkali metal or alkaline-earth metal soaps or soaps of organic bases. Use may be made, as fatty acids, of saturated, linear or branched fatty acids comprising from 8 to 30 carbon atoms and preferably comprising from 8 to 22 carbon atoms. This fatty acid may be chosen in particular from palmitic acid, stearic acid, myristic acid and lauric acid, and mixtures thereof.

Examples of basic agents that may be used include alkali metal hydroxides (sodium hydroxide and potassium hydroxide), alkaline-earth metal hydroxides (for example magnesium hydroxide), ammonium hydroxide or else organic bases, such as triethanolamine, N-methylglucamine, lysine and arginine.

The soaps may especially be fatty acid alkali metal salts, the basic agent being an alkali metal hydroxide and preferably potassium hydroxide (KOH).

The amount of basic agent must be sufficient for the fatty acid to be at least partially neutralized.

Preferably, the anionic surfactant(s) are chosen from alkyl sulfates, alkyl ether sulfates such as sodium lauryl ether sulfate, phosphates, alkylphosphates such as potassium cetylphosphate, amino acid derivatives, in particular sarcosine derivatives (sarcosinates), such as sodium cocoyl sarcosinate, soaps such as sodium stearate, carboxylic acids such as stearic acid, and mixtures thereof.

Preferentially, the anionic surfactant(s) are chosen from phosphates, alkylphosphates such as potassium cetylphosphate, sarcosine derivatives (sarcosinates), such as sodium cocoyl sarcosinate, soaps such as sodium stearate, carboxylic acids such as stearic acid, and mixtures thereof.

The non-ionic surfactants other than the non-ionic surfactants of formula (I) that may be present in the composition of the invention can be chosen in particular from alkyl polyglucosides (APGs), oxyalkylenated glycerol esters, oxyalkylenated fatty acid esters of sorbitan, polyoxyalkylenated (in particular polyoxyethylenated and/or polyoxypropylenated) fatty acid esters optionally in combination with a fatty acid ester of glycerol, such as the PEG-100 stearate/glyceryl stearate mixture sold for example by the company ICI under the name Arlacel 165, oxyalkylenated sugar esters, and mixtures thereof.

Use is preferably made, as alkyl polyglucosides, of those containing an alkyl group comprising from 6 to 30 carbon atoms and preferably from 8 to 16 carbon atoms and containing a glucoside group preferably comprising from 1.2 to 3 glucoside units. The alkylpolyglucosides may be chosen, for example, from decylglucoside (alkyl-C9/C11-polyglucoside (1.4)), for instance the product sold under the name Mydol 100 by the company Kao Chemicals or the product sold under the name Plantacare 2000 UP® by the company Cognis; caprylyl/capryl glucoside, for instance the product sold under the name Plantacare KE 3711® by the company Cognis; laurylglucoside, for instance the product sold under the name Plantacare 1200 UP® by the company Cognis; cocoyl glucoside, for instance the product sold under the name Plantacare 818 UP® by the company Cognis; caprylylglucoside, for instance the product sold under the name Plantacare 810 UP® by the company Cognis; and mixtures thereof.

The oxyalkylenated glycerol esters are especially polyoxyethylenated derivatives of esters of glycerol and of a fatty acid and of the hydrogenated derivatives thereof. These oxyalkylenated glycerol esters can be chosen, for example, from glyceryl esters of fatty acids which are hydrogenated and oxyethylenated, such as PEG-200 hydrogenated glyceryl palmate, sold under the name Rewoderm LI-S 80 by the company Goldschmidt; oxyethylenated glyceryl cocoates, such as PEG-7 glyceryl cocoate, sold under the name Tegosoft GC by the company Goldschmidt, and PEG-30 glyceryl cocoate, sold under the name Rewoderm LI-63 by the company Goldschmidt; oxyethylenated glyceryl stearates; and mixtures thereof.

The oxyalkylenated sugar esters are especially polyethylene glycol ethers of fatty acid and sugar esters. These oxyalkylenated sugar esters may be chosen, for example, from oxyethylenated glucose esters, such as PEG-120 methyl glucose dioleate, sold under the name Glucamate DOE 120 by the company Amerchol.

Preferably, the non-ionic surfactant(s) other than the non-ionic surfactants of formula (I) are chosen from oxyalkylenated glycerol esters and polyoxyalkylenated fatty acid esters optionally in combination with a fatty acid ester of glycerol.

Preferentially, the non-ionic surfactant(s) other than the non-ionic surfactants of formula (I) are chosen from PEG-200 hydrogenated glyceryl palmate, PEG-7 glyceryl cocoate and PEG-30 glyceryl cocoate, the PEG-100 stearate/glyceryl stearate mixture; and mixtures thereof.

The surfactant(s) can also be chosen from silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE 09® by the company Goldschmidt. One or more coemulsifiers, which may be chosen advantageously from the group comprising polyol alkyl esters, may also be added thereto.

Mention may also be made of non-silicone emulsifying surfactants, in particular alkyl esters or ethers of a polyol. As alkyl esters of a polyol, mention may in particular be made of polyethylene glycol esters, for instance PEG-30 dipolyhydroxystearate, such as the product sold under the name Arlacel P135® by the company ICI.

More preferentially, the additional surfactant(s) according to the invention are chosen from alkyl polyglucosides (APGs).

Preferably, the total content of the additional surfactant(s) optionally present in the composition according to the invention is between 0.01% and 20% by weight, more preferentially between 0.05% and 15% by weight, even more preferentially between 0.1% and 10% by weight, even better still between 0.2% and 5% by weight, relative to the total weight of the composition.

Preferably, when one or more additional non-ionic surfactant(s) are present, the total content thereof is less than that of the non-ionic surfactant(s) of formula (I).

The Polysaccharides

The composition according to the invention may optionally also comprise one or more polysaccharides.

Preferably, the composition according to the invention comprises one or more polysaccharides of lambda carrageenan type.

The polysaccharides of lambda carrageenan type may or may not be chemically modified. Preferably, the polysaccharides of lambda carrageenan type are not chemically modified.

Preferably, the molecular weight (MW) of the polysaccharide is between 100 000 and 10 000. Even more preferentially, the molecular weight is between 250 000 and 800 000.

By way of polysaccharide of lambda carrageenan type that may be present in the composition according to the invention, mention may be made of Satiagum UTC 10 from the company Degussa and Welgeenan ED 1039 from the company Eurogum.

Preferably, when it (they) is (are) present in the composition according to the invention, the polysaccharide(s) are present in a total content ranging from 0.01% to 20% by weight, preferably from 0.05% to 15% by weight, more preferentially from 0.1% to 10% by weight, better still from 0.2% to 5% by weight, relative to the total weight of the composition.

The Additives

The composition according to the invention may optionally also comprise one or more conventional additives well known in the art, such as natural or synthetic thickeners or viscosity regulators other than the fixing polymers and the polysaccharides described above and free of a cationic group; vitamins or provitamins; amphoteric or anionic polymers other than the fixing polymers described above; preservatives; non-cationic dyes; fragrances.

Those skilled in the art will take care to select the optional additives and the amount thereof such that they do not harm the properties of the composition of the present invention.

These additives are generally present in the composition according to the invention in an amount ranging from 0 to 20% by weight relative to the total weight of the composition.

The "base" composition represents a composition as previously described which does not comprise any propellant(s) as previously described.

The pH of said base composition generally ranges from 3 to 9, preferably from 3 to 7.5, preferentially from 3.5 to 7 and even better still from 4 to 6.8.

The pH of the base composition may be adjusted to the desired value by means of basifying agents or acidifying agents that are customarily used. Among the basifying agents, examples that may be mentioned include aqueous ammonia, alkanolamines, and mineral or organic hydroxides. Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

A subject of the invention is also an aerosol device comprising a composition according to the invention as previously described, a container containing said composition, and a means for spraying said composition.

Preferably, the aerosol device according to the invention makes it possible to spray said composition in the form of foam.

The composition according to the invention is advantageously packaged under pressure, in an aerosol device, for example a monobloc device, which comprises a spraying means and a container.

The spraying means is generally formed from a dispensing valve controlled by a dispensing head, which itself comprises a nozzle via which the composition of the invention is sprayed, preferably in mousse form.

The container containing the pressurized composition may be opaque or transparent. It may be made of glass, polymer or metal, and may optionally be coated with a protective varnish coat.

Preferably, the container of said aerosol device is transparent, such that the composition according to the invention is visible to the naked eye through said container.

Finally, a subject of the invention is a process for styling, that is to say shaping and/or fixing, keratin fibres, in particular human keratin fibres such as the hair, comprising the application to said fibres of the composition as previously described, this application being optionally followed by rinsing after an optional leave-on-time.

Preferably, the application of the composition according to the invention is not followed by rinsing.

In a first embodiment of the process according to the invention, the composition is applied to wet hair.

In a second embodiment of the process according to the invention, the composition is applied to dry hair.

The examples that follow serve to illustrate the invention without, however, being limiting in nature.

EXAMPLES

Example 1

The following composition A was prepared from the ingredients detailed in the table below, in which all the amounts are indicated as weight percentages of active material (AM) relative to the total weight of the composition.

| Ingredients | Content (weight % of AM) |
| --- | --- |
| OLETH-10 | 7.6 |
| DECYL GLUCOSIDE | 0.52 |
| LAMBDA-CARRAGEENAN | 0.95 |
| GLYCEROL | 0.95 |
| BENZYL ALCOHOL | 0.95 |
| GLUCOSE | 2.85 |
| PRESERVATIVES | qs |
| ISOBUTANE/PROPANE/BUTANE MIXTURE | 5 |
| DEIONIZED WATER | qs 100 |

Composition A above is clear, with a monophasic appearance, and has a turbidity of 24.4 NTU measured using a turbidimeter, model HI 88713-ISO from the company Hanna Instruments.

The monophasic appearance and the clarity of the composition are stable over time. In particular, after 2 months of storage at ambient temperature (25° C.), the appearance of the composition has not changed.

Composition A above was packaged in a pressurized aerosol device.

On spraying, a firm, creamy foam is obtained, which spreads easily on the head of hair and gives good styling and cosmetic properties, in particular with long-lasting fixing and a pleasant feel. The hair is soft, and has volume. The hairstyle obtained is natural, with no helmet effect.

Example 2

The following compositions were prepared from the ingredients detailed in the table below, in which all the amounts are indicated as weight percentages of active material (AM) relative to the total weight of the composition.

| | COMPOSITIONS | | | | |
| --- | --- | --- | --- | --- | --- |
| Ingredients | A1 | C1 | C2 | C3 | C4 |
| OLETH-10 | 14.25 | | | | |
| OLETH-5 | | 14.25 | | | |
| CETETH-10 | | | 14.25 | | |
| BEHENETH-10 | | | | 14.25 | |
| STEARETH-10 | | | | | 14.25 |
| ISOBUTANE/PROPANE/BUTANE MIXTURE | 5 | 5 | 5 | 5 | 5 |
| DEIONIZED WATER | qs 100 | qs 100 | qs 100 | qs 100 | qs 100 |

Composition A1 (invention) above is clear, with a monophasic appearance, this being the case even after 2 months of storage at ambient temperature (25°).

The turbidity of composition A1 is 4.19 NTU, measured using a turbidimeter, model HI 88713-ISO from the company Hanna Instruments.

Compositions C1, C3 and C4 (outside the invention) each exhibit an opaque white precipitate in suspension in the composition, whether a few seconds after preparing these compositions or after 24 hours of storage at ambient temperature (25° C.).

Composition C2 (outside the invention) exhibits two visually distinct phases, the upper phase of which is opaque, whether a few seconds after preparing the composition or after 24 hours of storage at ambient temperature (25° C.).

The invention claimed is:

1. A cosmetic composition having a monophasic appearance, comprising:
   i) at least one non-ionic surfactant of formula (I):

   $$R-O-(CH_2-CH_2-O)_n-H \qquad (I)$$

in which:
   R is a linear or branched $C_8$-$C_{40}$ alkenyl radical,
   n is an integer ranging from 6 to 20;
   ii) water; and
   iii) one or more propellants;
   wherein the composition does not comprise cationic polymer.

2. The composition according to claim 1, characterized in that the composition is free of cationic surfactant and/or of cationic silicone.

3. The composition according to claim 1, characterized in that R represents a linear or branched $C_{16}$-$C_{20}$ alkenyl radical, and/or n represents an integer ranging from 8 to 12.

4. The composition according to claim 1, characterized in that the at least one non-ionic surfactant of formula (I) is chosen from oleyl alcohol comprising 8 mol of ethylene oxide, oleyl alcohol comprising 10 mol of ethylene oxide, and oleyl alcohol comprising 12 mol of ethylene oxide.

5. The composition according to claim 1, characterized in that the total content of the at least one non-ionic surfactant of formula (I) is between 2.5% and 10% by weight, relative to the total weight of the composition.

6. The composition according to claim 1, characterized in that the one or more propellants are chosen from dimethyl ether, $C_3$-$C_5$ alkanes, and mixtures thereof.

7. The composition according to claim 1, characterized in that the total content of the one or more propellants is between 0.5% and 15% by weight relative to the total weight of the composition.

8. The composition according to claim 1, characterized in that the one or more propellants used are entirely dissolved or dispersed in the composition before the first use of the composition.

9. The composition according to claim 1, characterized in that it also comprises one or more fixing polymers chosen from vinyllactam homopolymers, vinyllactam copolymers, and mixtures thereof.

10. The composition according to claim 1, characterized in that it also comprises one or more oils chosen from $C_6$-$C_{16}$ alkanes, linear or branched hydrocarbons of mineral or synthetic origin containing more than 16 carbon atoms, non-silicone oils of animal origin, oils of plant origin, fluoro oils, liquid fatty alcohols, liquid fatty esters, non-salified liquid fatty acids, silicone oils, and mixtures.

11. The composition according to claim 10, characterized in that the total content of the one or more oils is between 3% and 25% by weight relative to the total weight of the composition.

12. The composition according to claim 1, characterized in that it also comprises one or more additional surfactants chosen from anionic surfactants, non-ionic surfactants other than the non-ionic surfactants of formula (I) as defined according to claim 1, and mixtures thereof.

13. An aerosol device comprising a composition as defined according to claim 1, a container containing said composition, and a means for spraying said composition.

14. The aerosol device according to claim 13, characterized in that it makes it possible to spray said composition in the form of foam.

15. The aerosol device according to claim 13, characterized in that the container is transparent.

16. A process for styling keratin fibres, comprising the application to said fibres of the composition as defined according to claim 1, this application being optionally followed by rinsing after an optional leave-on-time.

17. The composition according to claim 9, characterized in that the total content of the one or more fixing polymers ranges from 0.2% to 15% by weight relative to the total weight of the composition.

* * * * *